United States Patent [19]

Moore

[11] 4,235,253
[45] Nov. 25, 1980

[54] ELECTRIC DENTAL FLOSSER

[76] Inventor: Dawne A. Moore, Dallas, Tex.

[21] Appl. No.: 36,337

[22] Filed: May 7, 1979

[51] Int. Cl.³ .............................................. A61C 15/00
[52] U.S. Cl. .................................. 132/92 R; 433/114
[58] Field of Search ............. 128/62 A; 433/118, 142, 433/114; 132/92 R, 92 A

[56] References Cited

U.S. PATENT DOCUMENTS

| | | | |
|---|---|---|---|
| 2,788,000 | 4/1957 | Luther et al. | 128/62 A |
| 3,421,524 | 1/1969 | Waters | 132/92 R |
| 3,978,852 | 9/1976 | Annoni | 128/62 A |

Primary Examiner—Robert Peshock

[57] ABSTRACT

An electrically driven dental floss device having a tip with a forked end adapted to hold a short piece of dental floss tauntly across the forked end. A body handle having finger grips is adapted to move the forked end in a straight line motion vertically within a range of 1 to 2 millimeters such that the dental floss will move along side the tooth to clean such. A thumb button is provided to allow momentary energization by the elderly when using the device.

7 Claims, 7 Drawing Figures

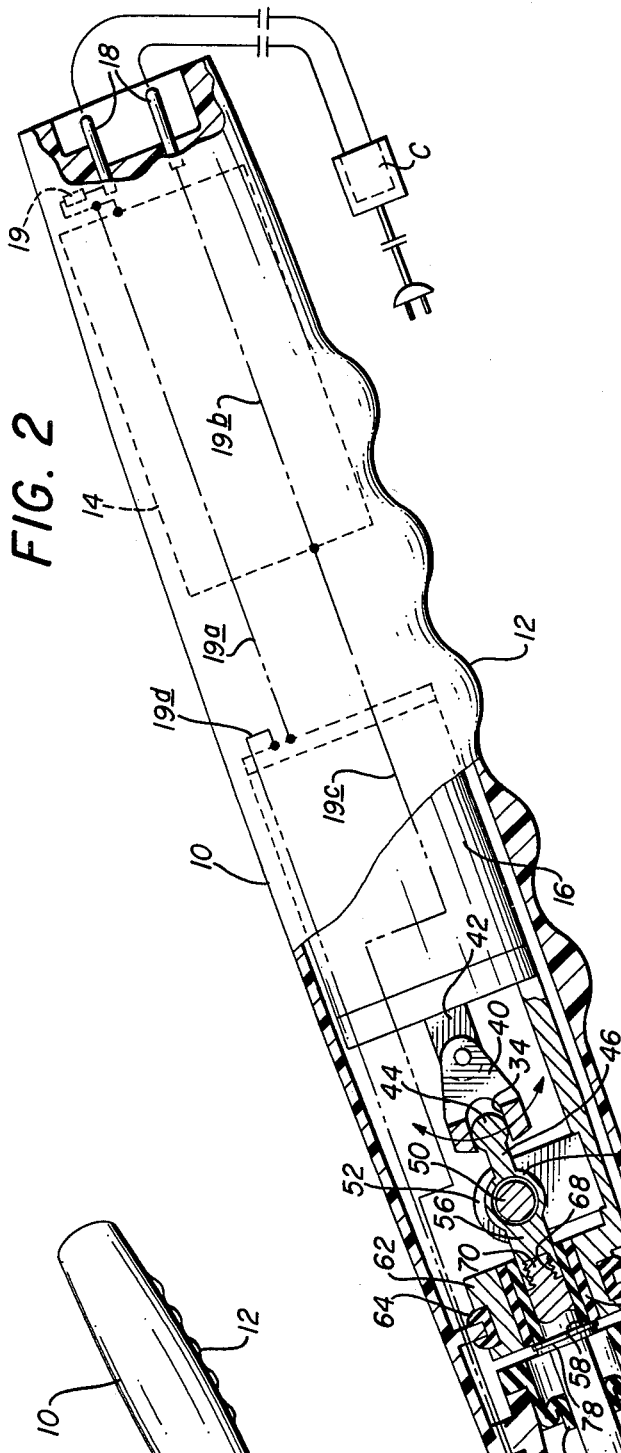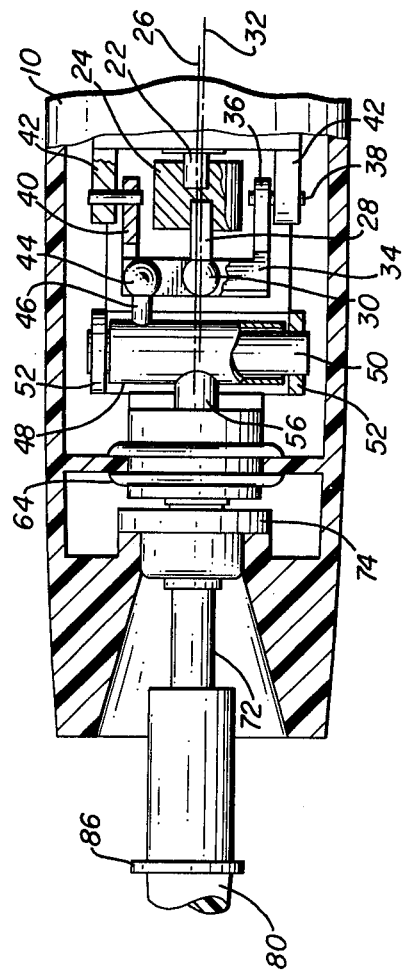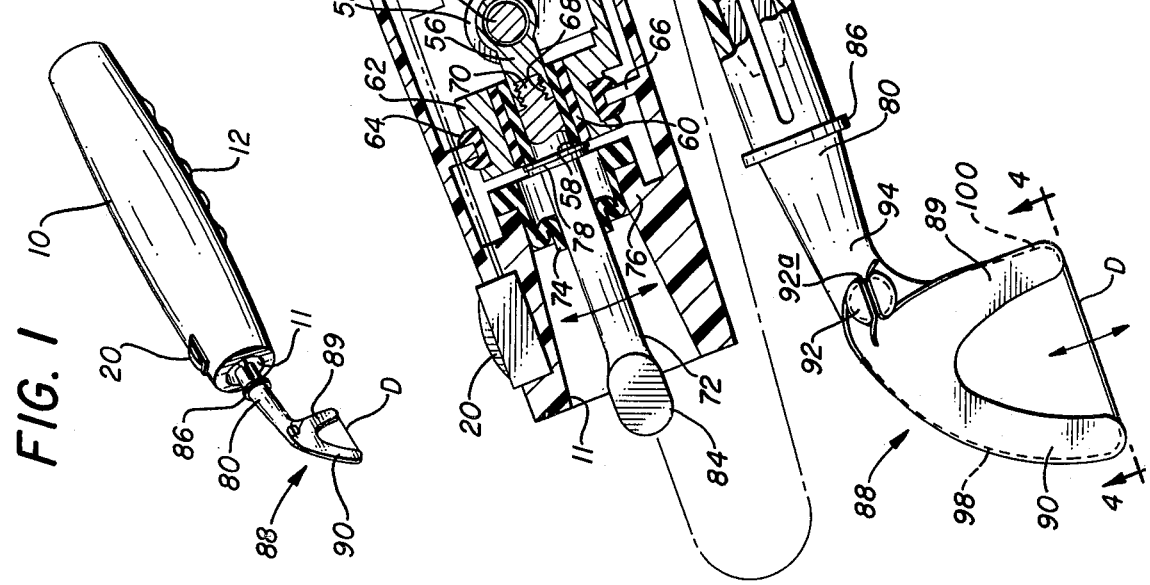

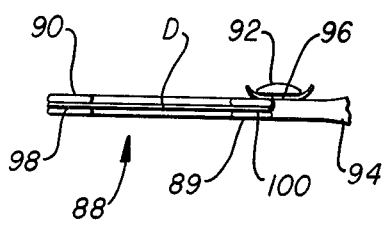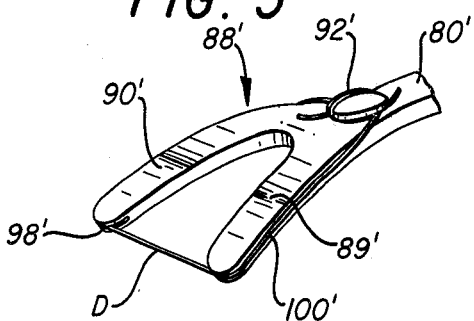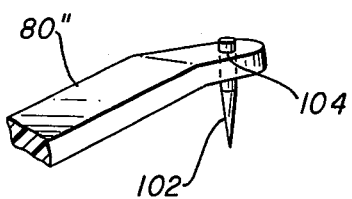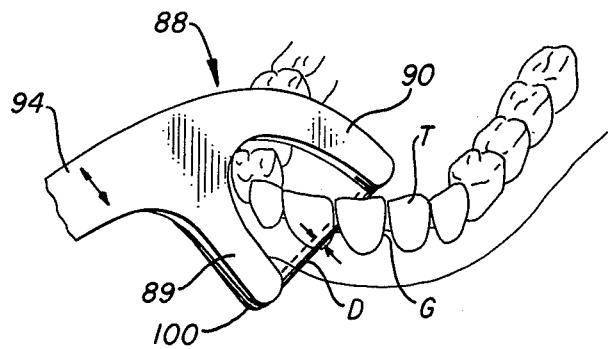

ELECTRIC DENTAL FLOSSER

BACKGROUND

This device is related to an electric dental floss device particularly adapted to be used by a handicapped person.

The handicapped persons having arthritis, rheumatism or physical impairments usually occurring in the aged are unable to properly clean their teeth with dental floss. Elderly persons suffer from a deteriorating of teeth and gums due to age and the inability to properly care for their teeth. The inability to use dental floss often results in serious dental decay and deterioration of the teeth and gums which results in a further loss of teeth causing pain and discomfort to the person, such as peridontal disease which is a major cause of tooth loss in adults.

The problems encountered by the elderly with flossing are the inability to manipulate the small dental floss between the teeth and then use the proper motion up and down the tooth on the sides and the back of the tooth to properly clean the plague and food material from behind and between the teeth.

Devices known to applicant to provide power driven dental cleaners are those such as disclosed in the patent to Waters, U.S. Pat. No. 3,421,524, which discloses an attachment to an electric toothbrush which provides oribital movement of dental floss in the end of the tip and distributed from a reel.

The patent to McCabe, U.S. Pat. No. 3,667,483, discloses a dental floss device which reciprocates the dental floss along the longitudinal axis of the length of the dental floss.

The patent to Warner, U.S. Pat. No. 3,759,274, discloses a device for using a strand of dental floss which reciprocates the dental floss between two ends which will move the floss transversely across the tooth.

The patent to Brien, U.S. Pat. No. 3,847,167, discloses a reciprocating dental floss device which moves the floss across the tooth and reciprocates it along the longitudinal axis of the floss.

To properly use dental floss, the dental floss must be taunt and movement must be up and down in a relatively vertical motion relative to the tooth.

SUMMARY

I have devised a power driven dental floss device having a tip on which a short strand of fresh dental floss is tightly secured across two outwardly extending forked ends of the tip. The tip is secured to an output shaft on a handle preferably having a finger grip for better control of the device by an arthritic person. The device is gripped in the hand and the thumb is placed over a normally open spring urged thumb button switch. The device is worked such that the dental floss moves between the teeth and the switch is depressed to energize a motor within the handle to move the tip in a reciprocating straight line up and down motion to move the floss upwardly and downwardly relative to the surface of the tooth. The length of the stroke vertically is limited to approximately one (1) or two (2) millimeters, thus preventing any harmful damage to the gingiva or gum. After sufficient time has been spent on that tooth, the device is turned off by lifting the thumb and it is moved to the next tooth. This provides a proper motion of the dental floss across the surface of the tooth for persons who have physical handicapps preventing them from moving the dental floss properly.

The primary object of the invention is to provide an electrically driven dental floss cleaner which moves the dental floss vertically along the surface of the tooth up and down to properly clean the tooth and remove plaque and food particles from behind and between the teeth having motion which will not damage the gingiva tissue and which is capable of being used by arthritic persons.

A further object of the device is to provide a device which can be used within nursing homes and the homes of elderly persons which provides a mechanical device for flossing their teeth in the proper manner to increase the life of the natural teeth thus preventing deterioration of the teeth and preventing peridontal disease.

It is a further object of the invention to provide a device which does not utilize a take-up spool adjacent the supply spool to maximize sanitary conditions and minimize infection due to unsanitary dispensement of dental floss.

Other and further objects of the invention will become readily apparent upon studying the detailed description and drawings attached hereto.

DESCRIPTION OF THE DRAWINGS

Drawings of a preferred embodiment are annexed hereto so that the invention may be better and more fully understood, in which:

FIG. 1 is a perspective view of the dental flosser;

FIG. 2 is a side elevational view with parts broken away to more clearly illustrate the details of construction of the dental flosser;

FIG. 3 is a top plan view thereof with parts broken away to more clearly illustrate the details of construction;

FIG. 4 is a cross-sectional view taken along line 4—4 of FIG. 2;

FIG. 5 is a perspective view of modified form of the flosser head;

FIG. 6 is a perspective view of a second modified form of the flosser head; and

FIG. 7 is an enlarged diagrammatic view of a tooth and surrounding gum area.

Numeral references are used to designate like parts throughout the various figures of the drawing.

DESCRIPTION OF THE PREFERRED EMBODIMENT

Referring to FIGS. 1-3 of the drawings, the electrically driven dental floss device generally comprises a housing 10 having a finger grip 12. The housing 10 generally comprises an elongated cylindrically shaped body that can be held within the hand and may be extruded from lightweight plastic or the like. A larger diameter housing 10 is preferred for handicapped persons; however, it should be appreciated that a smaller housing 10 without grips 12 may be used for non-handicapped persons.

A power source 14 such as a nickle cadmium battery may be enclosed within the housing 10 to drive the motor 16. Other sources of power may include the standard AC current or a dry cell battery. The nickle cadmium battery illustrated in the preferred embodiment may be connected to charging prongs 18 and charged by a transformer as is well known in the industry. Suitable wiring connections 19a, 19b, 19c and 19d as shown in the drawings are provided to connect the battery 14 to motor 16 through a normally open spring actuated thumb switch 20 and charging circuit 19 which is easily engageable by the thumb of the user to energize the unit. A suitable charger C is provided for charging the circuit.

The output shaft 22 of the motor 16 is connected to an adapter 24 which is aligned with the axis of rotation 26 of output shaft 22 of motor 16. The second shaft 28 has a ball-shaped head 30 and is positioned in the adapter 24 such that the longitudinal axis 32 of shaft 28 is offset from the axis of rotation 26 of the output shaft 22.

The ball 30 of shaft 28 is positioned in a slot 34 formed in yoke 36. Yoke 36 is pivotally secured by pin 38 through ears 40 to lugs 42 formed on opposed sides of the motor housing of motor 16. As the shaft 28 rotates, head 30 moves in a circular path slightly larger than the head 30 such that yoke 36 moves up and down the distance equal to twice the offset of the longitudinal axis 32 and axis of rotation 26. Yoke 36 is adapted to receive head 44 on shaft 46 in slot 34. Shaft 46 is secured on the outer end of sleeve 48. Sleeve 48 is pivotally secured on shaft 50 which is supported by lugs 52 on opposite ends of sleeve 48. A driven shaft 56 extends outwardly of sleeve 48 into a resilient sleeve 58 secured in a second resilient sleeve 60. Sleeves 58 and 60 are supported by a mounting 62 which is resiliently mounted by gomlet 64 in ears 66 of housing 10. A socket 68 is formed in the end of shaft 56 to receive end 70 of drive shaft 72. Shaft 72 is journaled through a resilient rubber seal 74 held in the end 76 of housing 10. A washer 78 engaging a groove to limit inward movement of shaft 72. An alternate method is to utilize a vibrator type motor for vertical movement.

The tip 80 generally comprises a plastic body having a socket 82 which fits on the square end 84 of shaft 72. The tip 80 has a ring 86 to prevent flow of fluids into the end 76 of the housing 10. The forked end 88 of tip 80 has two spaced legs 89 and 90 which extend out in a V-shaped arrangement. A short piece of dental floss designated D about 6–8 inches long is wound around a knob 92 which is spaced from the upper surface 94 of head 80 by shaft 96 a small distance. Dental floss is available in packages from various manufacturers. A first end of the dental floss D is wound around the knob 92 extends along a groove 98 along the edge of leg 90 across to a groove 100 formed in leg 89 and is wrapped around knob 92 again. This provides a means for tauntly securing the dental floss material D across the two legs 89 and 90 of the tip 80. The head 88 is positioned such that the dental floss D lies in a plane substantially transverse to the direction of movement of the floss. This embodiment of the tip 80 is particularly adapted to move between the front teeth.

A modified form of the tip 80 is illustrated in FIG. 5 and designated 80' and is substantially the same construction except that the forked end 88' is rotated 90° relative to the position of end 88 of tip 80. Tip 80' has a socket formed in one end to detachably secure the tip to shaft head 84.

A second modified tip 80" illustrated in FIG. 6 generally comprises a substantially elongated flat member having a hole 102 formed in one end to receive a toothpik 104 for cleaning along the gum line and between teeth. A socket is formed at the other end to detachably secure tip 80" to shaft head 84. The toothpik 104 moves vertically as it is moved the gingiva margin of each tooth both buccally and lingually to remove plaque from the teeth. Head 88' is positioned on the shaft of tip 80' such that the dental floss D lies in a plane substantially parallel to the direction of movement of the floss D. This embodiment of the tip 80' is particularly adapted to move between the rearmost or posterior teeth.

The operation of the hereinbefore described device is as follows:

A short piece of dental floss D is attached to the V-shaped head 88 or 88' as hereinbefore described. The tip 80 is placed on the electric flosser housing 10 by moving the socket 82 in the end of tip 80 onto head 84. Housing is gripped such that the thumb is placed over the thumb switch to activate the motor 16.

As the motor 16 is energized, output shaft 22 rotates rotating adapter 24. This in turn rotates shaft 28 which is off-centered and moves in a path which pivots yoke 36. This in turn moves head 44 up and down to rotate sleeve 48 on shaft 50. This moves shaft 56 up and down within the resilient bushing 58 and 60 and moves shaft 72 up and down. The end of head 80 will move vertically as shown by the arrows in FIGS. 2 and 7, such that the dental floss D moves in a vertical direction up and down. A slight arc may occur at the outer end of the tip 80 but this is negligible in that the majority of movement is straight line.

It is important to limit the range of motion of the dental floss D to between one and two millimeters (0.03937 to 0.07874 inches) vertically causing a small motion which will not damage the gingiva or the gum. As illustrated in FIG. 8, an enlarged tooth T is shown with the surrounding gum line or gingiva margin G. As the tip 80 is moved such that the dental floss D moves behind the tooth or between the teeth, it should be readily apparent that the dental floss D will move up and down on the side of the teeth at the gingiva margin G cleaning the buccal and lingual sides of the teeth as illustrated in FIG. 7. The limitation in movement is necessary to prevent damage to the soft gingiva of the gum which is extremely sensitive to large movements. The dental floss D is moved by the tip 80 or 80' parallel to the longitudinal axis of the teeth at the gingiva margin G to best clean the teeth.

By using different tips 80 and 80' the mesial buccal, mesial lingual, distal buccal and the distal lingual portions are cleaned on each tooth. Each side of the tooth can be safely cleaned. The dental floss D is moved between the teeth while the device is unenergized. Upon moving the dental floss D about the tooth with the forked head 88 or 88', the thumb switch is then depressed by the thumb and the device will move up and down thoroughly cleaning the tooth with a slight motion of the hand on the housing 10. When that side of the tooth is done the head is lifted to remove the dental floss D from the tooth and moved to the next tooth.

If desired the head 80" with the toothpik 102 in hold 102 may be used to clean between the tooth or at the gingival margin, in a vertical direction. When using tip 80", place end of the toothpik 104 at the gingival margin, turn device on and stay at the gingival margin of the tooth. This will remove plaque which has accumulated at the gingival margin. Tip 80" can be used on the buccal and lingual surfaces of the teeth.

It is the tauntness of the dental floss D, the vertical up and down motion of the floss D, and the sanitation of new dental floss which make this device particularly useful for the handicapped person.

It should be readily apparent from the foregoing that the invention hereinbefore discussed accomplishes each of the objects hereinbefore described in the invention.

It should be readily apparent that other and further embodiments of the invention may be devised without departing from the basic concept herein.

Having described my invention, I claim:

1. An electrically driven dental floss device comprising: a tip having a forked end; means to tauntly secure a short piece of dental floss across said forked end of said tip; a body handle; power means; switch means to momentarily energize said motor, an output shaft being adapted to detachably receive said tip; and connector means being adapted to connect said motor to said output shaft for moving said tip in a reciprocating straight line manner vertically relative to a tooth from a chewing surface of the tooth to under the gingival margin, the length of said reciprocating motion not to exceed two millimeters.

2. The combination called for in claim 1, wherein said switch means comprises: a thumb actuator on the open switch.

3. The combination called for in claim 1 wherein said body handle comprises: an elongated, substantially cylindrical shaped housing having molded finger grips for the hand to grasp; and said switch means being positioned to allow the thumb of the user to energize said motor.

4. The combination called for in claim 1 wherein said forked end on said tip comprises: a substantially V-shaped head being positioned such that the dental floss is positioned in a plane substantially transverse to the direction of movement of the dental floss; and a shaft securing said head to said connector means.

5. The combination called for in claim 1 including a tip comprising: a detachably elongated member being adapted to fit said output shaft, a small passage being formed in the end of the member; and a pointed member adapted to be positioned in said passage for cleaning between the teeth and at the gingival margin.

6. An electrically driven dental floss device comprising: a tip having a forked end; means to tauntly secure a short piece of dental floss across said forked end of said tip; a body handle; power means; switch means to momentarily energize said motor; an output shaft being adapted to detachably receive said tip; connector means being adapted to connect said motor to said output shaft for moving said tip in a reciprocating straight line manner vertically relative to a tooth, the length of said reciprocating motion not to exceed two millimeters, said forked end on said tip being a substantially V-shaped head being positioned such that the dental floss is positioned in a plane substantially parallel to the direction of movement of the dental floss; and a shaft securing said head to said connector means.

7. An electrically driven dental flosser device comprising: a tip having a substantially V-shaped head supported on the end of an elongated shaft; a groove formed along the peripheral edges of said V-shaped head; a knob positioned adjacent the forked end of the head adapted to receive an end of short piece of dental floss which is directed along the grooves on the peripheral edges of the tip across the tipped ends and back to the knob for securing the dental floss tauntly across the forked end of the tip; a body handle; power means to dispose of the said body handle; switch means to energize said motor; an output shaft being adapted to detachably receive said tip; and connector means being adapted to connect said motor of said output shaft for moving said tip in a reciprocating straight line manner vertically from a chewing surface on the upper portion of the tooth to under the gingival margin, the length of said reciprocating motion not to exceed two millimeters.

* * * * *